US009636304B2

(12) United States Patent
Guittet et al.

(10) Patent No.: US 9,636,304 B2
(45) Date of Patent: *May 2, 2017

(54) PHARMACEUTICAL COMPOSITION COMPRISING CITRATE AND BICARBONATE SALTS, AND USE THEREOF FOR TREATING CYSTINURIA

(75) Inventors: Catherine Guittet, Arles (FR); Luc-Andre Granier, Montfrin (FR); Caroline Roussel-Maupetit, Saint-Ismier (FR)

(73) Assignee: ADVICENNE, Nimes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/988,080

(22) PCT Filed: Nov. 18, 2011

(86) PCT No.: PCT/FR2011/052697
§ 371 (c)(1),
(2), (4) Date: May 17, 2013

(87) PCT Pub. No.: WO2012/066257
PCT Pub. Date: May 24, 2012

(65) Prior Publication Data
US 2013/0236545 A1 Sep. 12, 2013

(30) Foreign Application Priority Data

Nov. 18, 2010 (FR) ...................... 10 59474

(51) Int. Cl.
| | |
|---|---|
| A61K 9/20 | (2006.01) |
| A61K 33/00 | (2006.01) |
| A61K 31/194 | (2006.01) |
| A61K 9/28 | (2006.01) |
| A61K 31/215 | (2006.01) |
| A61K 31/717 | (2006.01) |
| A61K 31/745 | (2006.01) |
| A61K 33/06 | (2006.01) |
| A61K 33/10 | (2006.01) |
| A61K 45/06 | (2006.01) |
| A61K 9/48 | (2006.01) |

(52) U.S. Cl.
CPC .......... *A61K 9/2077* (2013.01); *A61K 9/2054* (2013.01); *A61K 9/2866* (2013.01); *A61K 31/194* (2013.01); *A61K 31/215* (2013.01); *A61K 31/717* (2013.01); *A61K 31/745* (2013.01); *A61K 33/00* (2013.01); *A61K 33/06* (2013.01); *A61K 33/10* (2013.01); *A61K 45/06* (2013.01); *A61K 9/2009* (2013.01); *A61K 9/2072* (2013.01); *A61K 9/4808* (2013.01)

(58) Field of Classification Search
None
See application file for complete search history.

(56) References Cited

U.S. PATENT DOCUMENTS

| | | | |
|---|---|---|---|
| 3,903,255 | A | 9/1975 | Gusman et al. |
| 4,451,454 | A | 5/1984 | Wong |

FOREIGN PATENT DOCUMENTS

| | | |
|---|---|---|
| DE | 2252665 A1 | 5/1973 |
| EP | 0429157 A2 | 5/1991 |
| EP | 1970066 A1 | 9/2008 |
| EP | 1 970 066 | 9/2009 |
| GB | 1403900 A | 8/1975 |
| GB | 2130087 A | 5/1984 |

OTHER PUBLICATIONS

K-Lyte product web page from <http://naturaldatabase.therapeuticresearch.com/nd/Search.aspx?pt=103&id=44110>.*
International Search Report dated Feb. 13, 2012, corresponding to PCT/FR2011/052697.
David S. Goldfarb: "Urinary Alkalization"; Cystinuria Support Network Internet Article, Sep. 27, 2008; pp. 1-3.
C.S. Biyani, et al.; "Cystinuria—Diagnosis and Management"; vol. 4, No. 5; Oct. 1, 2006; pp. 175-183.
Anonymous: "Patient Handout Potassium BiCarbonate and Potassium Citrate K-Lite"; Mescape; May 1, 2010; XP-002648918.
Breitkreutz et al., "Enteric-coated solid dosage forms containing sodium bicarbonate as a drug substance: an exception from the rule?", Journal of Pharmacy and Pharmacology, 2007, vol. 59, pp. 59-65.
Information professionelle sur Nephrotrans, open drug database, ch.oddb.org.
Harvey et al., "Bioavailability of citrate from two different preparations of potassium citrate", The Journal of Clinical Pharmacology, 1989, vol. 29, pp. 338-341.
Hess, B., "Erreus pathophysiologiques, Investigations simples/extensives, role de l'alimentation, medicaments et pathologie lithiasique renale—ou se situe l'evidence?", Forum Med. Suisse, 2001, No. 45, pp. 1119-1127.

(Continued)

Primary Examiner — Patricia Duffy
Assistant Examiner — Garen Gotfredson
(74) Attorney, Agent, or Firm — Browdy and Neimark, PLLC

(57) ABSTRACT

A solid oral pharmaceutical composition in the form of tablets including:—a first solid oral pharmaceutical formulation in the form of at least one micro-tablet, the micro-tablet consisting of a core including at least one Krebs cycle precursor salt as active ingredient, and of a coating including at least one coating agent, and—a second oral pharmaceutical formulation in the form of at least one mini-tablet, the mini-tablet consisting of a core including at least one bicarbonate salt as active ingredient and at least one prolonged-release matrix, and of a coating including at least one coating agent. The use thereof as a medicament, in particular in the treatment and/or prevention of cystinuria.

16 Claims, 4 Drawing Sheets

(56) References Cited

OTHER PUBLICATIONS

Wolffram et al., "Transport of Tri- and Dicarboxylic Acids Across the Intestinal Brush Border Membrane of Calves", The Journal of Nutrition, 1990, vol. 120, pp. 767-774.

English translation of Product form: Nephrotrans, Treatment of acidosis, Information professionelle sur Nephrotrans, open drug database, ch.oddb.org, pp. 1-2.

* cited by examiner

PHARMACEUTICAL COMPOSITION COMPRISING CITRATE AND BICARBONATE SALTS, AND USE THEREOF FOR TREATING CYSTINURIA

The present application relates to a pharmaceutical composition comprising citrate salt and bicarbonate salt, which can be used as a medicament in particular for treating cystinuria.

Cystinuria, which affects one in 7000 people worldwide, is a hereditary disorder involving transport of the dibasic amino acids cystine, ornithine, lysine and arginine. This transport disorder is generally reflected in excessive urinary excretion and a disorder of intestinal absorption of cystine.

Cystine lithiasis is the only clinical manifestation of cystinuria. It represents from 1 to 3% of lithiases in adults and from 6 to 8% of lithiases in children.

The seriousness of the disease arises from the fact that cystine has very low solubility in urine, as the lack of digestive absorption of these amino acids has no clinical consequence. Supersaturation of the urine with cystine induces the formation of crystals, and cystine calculi are created. There is no known inhibitor of cystine crystallization.

The solubility of cystine depends on the pH of the urine. The higher and more alkaline the pH, the more the cystine is in a soluble form.

The aim of the medical treatment of cystinuria is to keep the urine under-saturated with cystine. This is generally achieved by at least one of the following actions:
  lowering the urinary cystine concentration with a low-methionine and low-sodium diet, and by dilution of the urine: a volume of urine of at least 3 liters per day is required for dissolving all the cystine. This treatment requires a regular distribution of drinks throughout the 24-hour period and especially at night.
  increasing the solubility of cystine by alkalization of the urine, so as to keep the urinary pH constantly at alkaline values (greater than or equal to 7.0).

None of the various actions are completely effective on its own. In case of failure, these measures are supplemented by prescribing a sulphydrylated compound, preferably tiopronin.

Various citrate-based or bicarbonate-based compositions are used for alkalizing the urine of patients with cystinuria:
  Vichy water comprising sodium bicarbonate but which can lead to exposure to fluorosis;
  potassium citrate, providing the same alkalization as bicarbonate without increasing natriuresis. It should be prescribed at a dosage from 6 to 8 g/day diluted in 1.5 to 2 liters of water. Gastric tolerance of potassium citrate is mediocre and the palatability of the pharmaceutical forms is poor.

Alkalization as currently practiced consists of absorption of doses of citrate or doses of bicarbonate, multiple times, day and night, owing to their brief efficacy.

Thus, alkalization with sodium bicarbonate at a dosage from 8 to 16 grams per day (g/d) in adults, well distributed over the 24-hour period in 2 to 3 liters of water, reflects one practice. Higher doses (30 to 40 g/d) of sodium bicarbonate theoretically make it possible to maintain urinary pH constantly above 7.0 or even in certain cases to reach a pH of 7.5, but their gastric tolerance is mediocre.

The existing pharmaceutical forms are far from providing optimum alkalization, even with good adherence to the treatment. At present it is impossible to maintain the urinary pH above 7 continuously. In fact, the commercial pharmaceutical forms assume administration every two hours, including at night. This represents a major constraint, which patients find difficult to accept in the medium or long term.

Moreover, each of these compositions of salts has low gastrointestinal tolerance, which is another drawback in using them and limits the dose per administration.

At present, the only example of a combination of these two salts in a single formulation is the medicament marketed in the form of effervescent tablets under the name Kalium Hausmann Effervettes®, each tablet comprising 1700 mg of potassium citrate and 1440 mg of potassium bicarbonate. This formulation does not, however, solve the problems described above, since the two active ingredients are released at the same time, and immediately. In particular, the gastric tolerance of these tablets is very poor. Moreover, Kalium Hausmann Effervettes® is not indicated in cystinuria, but in potassium deficiency.

The purpose of the present invention is therefore to propose a composition that solves the many problems of the compositions of the prior art, and in particular makes it possible, with a moderate number of daily administrations, for example two, to keep the patient's urinary pH at an alkaline value, greater than or equal to 7.

Thus, the applicant has developed a solid pharmaceutical composition for oral use in the form of tablets comprising:
  a first solid pharmaceutical formulation for oral use in the form of at least one microtablet, the microtablet being constituted by a core comprising at least one Krebs cycle precursor salt as active ingredient, preferably as the only active ingredient, and a coating comprising at least one coating agent,
  and
  a second pharmaceutical formulation for oral use in the form of at least one mini-tablet, the mini-tablet being constituted by a core comprising at least one bicarbonate salt as active ingredient, preferably as the only active ingredient, and at least one sustained-release matrix, and a coating comprising at least one coating agent.

Preferably, the microtablet of the first pharmaceutical formulation consists of a core and a coating.

Preferably, the mini-tablet of the second pharmaceutical formulation consists of a core and a coating.

The two pharmaceutical formulations are different from one another. The composition according to the invention is an alkalizing pharmaceutical composition, which can be administered orally, comprising Krebs cycle precursor salt, preferably citrate salt, and bicarbonate salt, and which presents notable improvements relative to the compositions known from the prior art. The first and second formulations are administered to the patient simultaneously, but their pharmacokinetic and pharmacological effects are complementary and are independently and temporally delayed.

One of the advantages of the composition of the invention is that it is long-acting. In fact, it was found in three subjects that urinary pH was maintained at recommended values (pH between 7.0 and 8.0) over a period of several hours, and ideally for a duration of 8 hours in order to cover the whole night. This advantageously relieves patients of the inconvenience of having to wake up during the night and drink an alkalizing solution in order to alkalize their urine continuously.

Another advantage of the composition according to the invention is better gastric tolerance, and easier adjustment of the doses.

Moreover, the composition according to the invention is easy to swallow and has an acceptable taste.

Finally, the composition according to the invention makes it possible to avoid assaulting the body with an abrupt proximal alkaline overload of the active ingredients, by distributing their loading gradually all along the intestine. Consequently the efficacy of the composition according to the invention throughout the 24-hour period is better than that of the compositions according to the prior art.

In a preferred embodiment, the composition consists of a first formulation and a second formulation, i.e. it does not comprise any other component apart from these two formulations.

Preferably, the composition comprises from 30 to 70% of first formulation and from 70 to 30% of second formulation, by weight relative to the total weight of the composition. As an example, the composition comprises 33% of first formulation and 67% of second formulation, by weight relative to the total weight of the composition.

Mixing of first-formulation microtablets and of second-formulation mini-tablets is generally carried out in such a way as to ensure homogeneous distribution of these two formulations throughout the composition. Thus, the composition preferably comprises a homogeneous distribution of the two formulations within it, i.e., for example for a composition with 50% of the first formulation and 50% of second formulation, a tablet selected at random has equal probability of being a first-formulation tablet as of being a second-formulation tablet.

Each of the micro- and mini-tablets according to the invention is coated. According to the definition of the European Pharmacopoeia (Ph. Eur.), a coated tablet is a tablet covered with one or more layers of mixture of various substances such as natural or synthetic resins, gums, gelatin, insoluble inert fillers, sugars, plasticizers, polyols, waxes, colourants permitted by the competent authority and, sometimes, flavourings and active ingredients. However, according to the invention, it is excluded for the coating to comprise an active ingredient, whether a Krebs cycle precursor salt or a bicarbonate salt.

When the coating consists of a very thin polymer film, the tablet is called film-coated (cf. Ph. Eur.).

Advantageously, the coating makes it possible both to mask the taste and to control the release kinetics of the active ingredient contained in the coated tablet.

The "tablet core" is, according to the invention, the whole tablet excluding the coating.

By "pharmaceutical composition" is meant, according to the invention, a composition the components of which are acceptable from a pharmaceutical standpoint. In particular, the composition consists of components that are suitable and acceptable for oral pharmaceutical administration. Consequently, each of two pharmaceutical formulations also consists of components that are suitable and acceptable for oral pharmaceutical administration.

By "component selected from the elements" is meant that the component is one of the elements or is a mixture of these elements.

This controlled release observed in vitro (separately) both for the first formulation and for the second formulation, reflects the controlled release of these two formulations, and therefore of the composition, in the body. Said release is described as "sustained" because it reaches or exceeds a duration of one hour.

This controlled release observed in vitro reflects controlled release in the body, which can be verified by measuring the urinary pH of subjects treated with this composition, usually at regular intervals, for example every two hours.

First Pharmaceutical Formulation

By "Krebs cycle precursor salt" is meant, according to the invention, at least one salt selected from fumarates, malates, citrates, alpha-ketoglutarate, succinyl CoA (or succinyl-coenzyme A), succinates and oxaloacetate. These salts all play a role in the Krebs cycle.

The Krebs cycle precursor salt is particularly preferably a citrate salt.

The citrate salt is preferably selected from potassium citrate, sodium citrate and magnesium citrate, and even more preferably the citrate salt is potassium citrate.

The first pharmaceutical formulation according to the invention very advantageously permits continuous, controlled release in vivo of the Krebs cycle precursor salt, after a single administration, for a time generally of four hours at most. Continuous release means, according to the invention, release that takes place constantly in vivo, from the single administration of the composition up to a time of about four hours at most.

Preferably, the first pharmaceutical formulation according to the invention is such that it releases in vivo practically all of the Krebs cycle precursor salt (i.e. at least 95% of said salt) over a maximum time of about four hours after a single administration of the composition.

According to a preferred variant, the first formulation according to the invention is able to release (or dissolve) the Krebs cycle precursor salt in vitro in a dissolution medium of purified water at pH 7 carried out with a dissolution apparatus of type 2, according to the European Pharmacopoeia (Ph. Eur.) 2.9.3 "Dissolution test for solid dosage forms", at a rate of from 2% to 15% in 15 minutes, from 15% to 25% in 30 minutes, and from 30% to 50% in one hour.

This pH of 7 is a measurement that is easily performed in the laboratory, as it is the pH of purified water. The measurement is therefore simply carried out by dissolution in purified water.

According to a preferred variant, the first formulation according to the invention is able to release (or dissolve) the Krebs cycle precursor salt in vitro in a dissolution medium of solution buffered at pH 1.3 carried out with a dissolution apparatus of type 2, according to the European Pharmacopoeia (Ph. Eur.) 2.9.3 "Dissolution test for solid dosage forms", at a rate of from 2% to 15% in 15 minutes, from 15% to 25% in 30 minutes, and from 30% to 50% in one hour.

This pH of 1.3 is representative of the acidic medium of the stomach.

For these measurements, one gram of first pharmaceutical formulation, which corresponds to a unit dose, is placed in a dissolution apparatus of the Pharmatest type, model PTW S3C, in which the temperature conditions are 37° C.±0.5° C., and the rotary speed is 100 rpm (revolutions per minute). The volume of the dissolution vessel is 1 L and the dissolution medium used is purified water at pH 7 or a solution buffered at pH 1.3.

The Krebs cycle precursor salt, and in particular the citrate salt, is analysed as is known by a person skilled in the art. For example, the potassium citrate released is quantified with a flame photometer, the analytical method having been validated according to the ICH recommendations CPMP/ICH/381/95-ICH Q2 (R1).

Preferably, the Krebs cycle precursor salt is completely dissolved (degree of dissolution of 100%) in about four hours, whether the pH is 7 or 1.3.

The first formulation according to the invention comprises usually from 40% to 80%, preferably from 50 to 70%, by weight Krebs cycle precursor salt based on the total weight of the first formulation.

The Krebs cycle precursor salt is thus present in a dose that is physiologically effective or represents a multiple or a sub-multiple of an effective dose for a standard patient.

The coating agent of the first-formulation microtablet is generally selected from alginates, carboxyvinyl polymers, sodium salts of carboxymethyl cellulose, cellulose derivatives including the polymers hydroxypropyl methylcellulose, hydroxypropyl ethylcellulose, hydroxypropyl cellulose, hydroxyethyl cellulose, methyl cellulose, ethyl cellulose, xanthan gum and polyethylene oxide, waxes such as paraffin wax, beeswax or carnauba wax, ammonium methacrylate copolymers of type A and B as described in the European Pharmacopoeia, and the polyacrylates of about 30% dispersion as described in the European Pharmacopoeia. Preferably, according to the invention, the coating agent is an ethylcellulose polymer.

According to one embodiment of the invention, the coating comprises, in addition to a coating agent such as selected from the above list, a flavouring agent and/or a colourant.

The thickness and homogeneity of the coating is an important parameter of the invention, as it influences the diffusion of the Krebs cycle precursor salt through the coating and therefore the dissolution kinetics of said salt. Selection of the nature and of the amount of the coating agent used is also an important parameter of the invention.

The first pharmaceutical formulation according to the invention generally comprises from 0.01% to 5%, preferably from 0.01% to 2% by weight, even more preferably from 1.4 to 2.5%, coating agent of the first-formulation microtablet relative to the total weight of the first formulation.

The first pharmaceutical formulation according to the invention can further comprise:

from 10% to 40%, preferably from 25% to 35% by weight, relative to the total weight of the first formulation, of a binder selected from microcrystalline celluloses, polyvidone, polyvinylpyrrolidone, copovidone, shellac, gelatin, polymethacrylates, synthetic resins, acrylates, maltodextrin, and starches, and preferably the binder comprises at least one microcrystalline cellulose;

from 0.01% to 5%, preferably from 0.02% to 3% by weight, relative to the total weight of the first formulation, of a flow agent (or lubricant) selected from stearic acid, polyethylene glycol, magnesium stearate, calcium stearate, zinc stearate, talc, silica, hydrogenated castor oil, glyceryl behenate, and glyceryl palmitostearate, and preferably the flow agent is selected from magnesium stearate and glyceryl behenate; and/or any suitable pharmaceutical excipient, in a quantity used conventionally in the field in question, for example from 0.0001% to 20% of the total weight of the composition.

The first-formulation pharmaceutical excipient is generally inert, i.e. inactive and non-toxic, and acceptable from a pharmaceutical standpoint. Such an excipient is most often selected from diluents, binders, disintegrants, flow agents, lubricants, colourants permitted by the competent authority, dispersants, solubilizers, stabilizers, preservatives, plasticizers and flavouring agents. Such an excipient can also be a support, for example selected from the group comprising celluloses such as hydroxymethylcellulose, carboxymethylcellulose, cyclodextrins, polysorbate 80, mannitol, gelatin, lactose, vegetable oils, animal oils, carbonates, starches and acacia.

Moreover, the first formulation according to the invention can comprise at least one matrix agent, present in the core of the microtablet, generally as a sustained-release matrix, preferably with a content comprised within a range of from 10% to 30%, even more preferably from 15% to 25%, by weight relative to the total weight of the composition. Said matrix agent is preferably selected from the coating agents mentioned above.

The European Pharmacopoeia (Ph. Eur.) defines, among tablets with modified release, sustained-release tablets, delayed-release tablets and sequential-release tablets. Modified-release tablets are tablets, coated or uncoated, that are prepared with special excipients, or by particular methods, or both, with the aim of modifying the rate, the place or the moment of release of the active ingredient(s).

In general, sustained-release tablets are tablets permitting release of an active ingredient that is sustained over time and according to defined kinetics. This is preferably achieved by making a tablet core, or a plain tablet (i.e. uncoated) using a sustained-release matrix containing the active ingredient(s). A sustained-release matrix is generally a matrix system, most often a network polymer, whether hydrophilic or lipophilic. The diffusion of the active ingredient(s) within this network is generally influenced not only by the intrinsic physicochemical properties of this or these active ingredient(s) (such as solubility, molecular weight etc.), but also by those characterizing the matrix network (such as: hydrophilicity, degree of polymerization, gelling rate, erosion).

The European Pharmacopoeia (Ph. Eur.) defines a tablet as a solid preparation containing a unit dose of one or more active substances. Tablets are obtained by agglomerating a constant volume of particles by compression, or by some other suitable method of manufacture such as extrusion, moulding or freeze-drying (lyophilization). Tablets are intended to be administered orally. Tablets are generally in the form of a right cylinder, the lower and upper faces of which can be flat or convex and the edges bevelled. The size of a tablet, or average dimension, is therefore generally the diameter of this cylinder, or an equivalent. However, if the height of the cylinder is significant, and greater than the diameter of the cylinder, the size of the tablet is the height of this cylinder.

By "microtablet" is meant, according to the invention, a tablet with a size comprised within a range from 2 to 4 mm (generally with the size accurate to ±10%). Preferably, all the microtablets of the first formulation have substantially the same composition and have a similar dissolution rate, which is the dissolution rate that can characterize the first pharmaceutical formulation of the invention. This dissolution rate is commonly established on the basis of one unit of the preparation, or in the context of the invention, one gram of microtablets.

The first-formulation microtablets according to the invention are coated, which makes it possible to mask the taste.

According to one embodiment of the invention, the first formulation comprises from 55% to 70% of potassium citrate, from 20 to 30% of microcrystalline cellulose, from 0.02% to 2% of magnesium stearate, from 0.01% to 1% of glyceryl behenate and from 1 to 3% of ethyl cellulose, relative to the total weight of the first formulation.

Second Pharmaceutical Formulation

The bicarbonate salt is preferably selected from potassium bicarbonate, sodium bicarbonate and magnesium bicarbonate, and even more preferably the bicarbonate salt is potassium bicarbonate.

The second pharmaceutical formulation advantageously permits controlled passage of the bicarbonate salt through the intestinal tract, sustained over at least 2 hours, preferably over at least 6 to 8 hours, even more preferably over 8 hours.

The second pharmaceutical formulation according to the invention very advantageously permits sustained, continuous release in vivo of the bicarbonate salt after taking a single dose, i.e. a single administration, over a long time, generally after a quarter of an hour and up to twelve hours, in a sustained manner. Release generally begins shortly after this single administration, or most often starting from a quarter of an hour after this administration, although release can begin immediately after administration. By continuous release is meant, according to the invention, a release that takes place constantly in vivo, from the time the composition is taken up until the time of about twelve hours. The kinetics of said release is generally close to zero-order kinetics. Such a release is described as "sustained" because it reaches or exceeds a duration of one hour.

Preferably, the second pharmaceutical formulation according to the invention is such that it releases in vivo the majority of the bicarbonate salt (i.e. at least 50% of said salt) over a time of between eight and twelve hours after a single administration of the composition.

Without wishing to be bound by any hypothesis, the applicant thinks that the mechanism of action is such that, when the second formulation is administered orally to a subject, the release of the active ingredient is controlled and sustained: the bicarbonate salt is absorbed along the whole digestive tract.

Advantageously, the gastric tolerance of the second formulation is improved relative to the compositions known from the prior art. In fact, as release of the bicarbonate salt generally takes place over more than eight hours, there is no intolerance to potassium or alkalosis on administration of the dose. Therefore there are no side-effects associated with metabolic alkalosis or digestive disorders, such as diarrhoea.

According to a preferred variant, the second formulation according to the invention is able to release (or dissolve) the bicarbonate salt in vitro in a dissolution medium of purified water at pH 7 with a dissolution apparatus of type 2, according to the European Pharmacopoeia (Ph. Eur.) 2.9.3 "Dissolution test for solid dosage forms", at a rate of at most 50% in 4 hours, at most 75% in 6 hours, and at most 90% in 8 hours.

More preferably, according to the invention, independently or not of the preceding variant, the second formulation according to the invention is able to release or dissolve the bicarbonate salt in vitro in a dissolution medium of purified water at pH 7 with a dissolution apparatus of type 2, according to the European Pharmacopoeia (Ph. Eur.) 2.9.3 "Dissolution test for solid dosage forms", at a rate comprised within a range from 5% to 15% in one hour, at a rate in the range from 35% to 55% in five hours, and at a rate comprised within a range from 70% to 90% in ten hours.

This pH of 7 is a measurement that is easily performed in the laboratory, as it is the pH of purified water. The measurement is therefore simply carried out by dissolution in purified water.

According to a preferred variant, the second formulation according to the invention is able to release (or dissolve) the bicarbonate salt in vitro in a dissolution medium of solution buffered at pH 1.3 with a dissolution apparatus of type 2, according to the European Pharmacopoeia (Ph. Eur.) 2.9.3 "Dissolution test for solid dosage forms", at a rate of at most 50% in 4 hours, at most 75% in 6 hours, and at most 90% in 8 hours.

Especially preferably according to the invention, independently or not of the preceding variant, the second formulation according to the invention is able to release (or dissolve) the bicarbonate salt in vitro in a dissolution medium of solution buffered at pH 1.3 with a dissolution apparatus of type 2, according to the European Pharmacopoeia (Ph. Eur.) 2.9.3 "Dissolution test for solid dosage forms", at a rate comprised within a range from 5% to 15% in one hour, at a rate in the range from 35% to 55% in five hours, and at a rate comprised within a range from 70% to 90% in ten hours.

In general, dissolution of the second formulation according to the invention in vitro in a given dissolution medium, according to the conditions described above, is independent of the pH. This means that, whatever the pH of the dissolution medium within a range between 1.3 and 7, dissolution takes place according to the same kinetics. In this case the applicant selected two different dissolution media, each characterized by its own pH, namely pH 1.3 and pH 7, for defining this profile in a characteristic manner, according to a test that is easily reproducible in vitro.

The dissolution test of the bicarbonate salt is carried out under the same conditions as the dissolution test of the Krebs cycle precursor salt.

The bicarbonate salt is quantified as is known to a person skilled in the art. For example, the potassium bicarbonate released is quantified by conductometry, the analytical method having been validated according to the ICH recommendations CPMP/ICH/381/95-ICH Q2 (R1).

In the composition according to the invention, the bicarbonate salt preferably does not begin to dissolve until after a quarter of an hour (dissolution rate generally close to about 0%), then the dissolution kinetics is almost of zero order.

The second formulation according to the invention most often comprises from 40% to 80%, preferably from 50 to 80%, for example from 50 to 70%, by weight bicarbonate salt based on the total weight of the second formulation.

The coating agent of the second-formulation mini-tablet is generally selected from alginates, carboxyvinyl polymers, sodium salts of carboxymethyl cellulose, cellulose derivatives including the polymers hydroxypropyl methylcellulose, hydroxypropyl ethylcellulose, hydroxypropyl cellulose, hydroxyethyl cellulose, methyl cellulose, ethyl cellulose, xanthan gum and polyethylene oxide, waxes such as paraffin wax, beeswax or carnauba wax, ammonium methacrylate copolymers of type A and B as described in the European Pharmacopoeia, and the polyacrylates of about 30% dispersion as described in the European Pharmacopoeia. Preferably, according to the invention, the coating agent is an ethylcellulose polymer.

According to the invention, the coating preferably comprises, in addition to a coating agent such as selected from the above list, a flavouring agent, and a colourant.

The thickness and homogeneity of the coating is one of the essential parameters of the invention, as it influences the diffusion of the bicarbonate salt through the coating and therefore the dissolution kinetics of this salt. Selection of the nature and of the amount of the coating agent used is also an important parameter of the invention.

The second pharmaceutical formulation according to the invention generally comprises from 1% to 20%, preferably from 1.5% to 3% by weight coating agent of the second-formulation mini-tablet relative to the total weight of the second formulation.

The sustained-release matrix of the second formulation is generally a hydrophilic matrix, i.e. is formed from a material that can undergo gelling and absorb an aqueous medium, or an inert matrix, i.e. a matrix comprising excipients belonging essentially to the class of thermoplastic polymers; these polymers are generally inert with respect to biological tissues, other excipients in the formulation and the active ingredient, and they are insoluble and non-digestible in the fluids of the gastrointestinal tract. More preferably, said sustained-release matrix of the second formulation is selected from alginates, carboxyvinyl polymers, sodium salts of carboxymethyl cellulose, cellulose derivatives including the polymers hydroxypropyl methylcellulose, hydroxypropyl ethylcellulose, hydroxypropyl cellulose, hydroxyethyl cellulose, methyl cellulose, ethyl cellulose, and the polyacrylates with dispersion of about 30% as described in the European Pharmacopoeia, and even more preferably this sustained-release matrix is a hydroxypropyl methylcellulose.

The second pharmaceutical formulation according to the invention generally comprises from 10% to 30%, preferably from 15 to 25% by weight sustained-release matrix of the second-formulation mini-tablet relative to the total weight of the second formulation.

The second pharmaceutical formulation according to the invention can further comprise:

from 5% to 20%, preferably from 5% to 10% by weight, relative to the total weight of the second formulation, of a binder selected from microcrystalline celluloses, polyvidone, polyvinylpyrrolidone, copovidone, shellac, gelatin, polymethacrylates, synthetic resins, acrylates, maltodextrin, and starches, and preferably the binder comprises at least one microcrystalline cellulose;

from 0.01% to 5%, preferably from 0.01% to 3% by weight, relative to the total weight of the second formulation, of a flow agent selected from stearic acid, polyethylene glycol, magnesium stearate, calcium stearate, zinc stearate, talc, silica, hydrogenated castor oil, glyceryl behenate, and glyceryl palmitostearate, and preferably the flow agent is magnesium stearate; and/or any suitable pharmaceutical excipient, in an amount used conventionally in the field in question, for example from 0.0001% to 20% of the total weight of the second formulation.

The second-formulation pharmaceutical excipient is selected, independently of the pharmaceutical excipient of the first formulation, in the same way as the first-formulation excipient.

Preferably, all the mini-tablets have the same composition and have a similar dissolution rate, which is the dissolution rate that can characterize the second pharmaceutical formulation of the invention.

The second pharmaceutical formulation is in the form of mini-tablets.

By "mini-tablet" is meant, according to the invention, a tablet with a size of at least 2 mm, for example comprised within a range from 2 to 25 mm (generally with the size accurate to ±10%). A person skilled in the art is able to select the tablet size. These tablets can be microtablets, or tablets of a larger size, for example comprised within a range from 4 to 25 mm. According to a preferred embodiment of the invention, the second-formulation mini-tablet is preferably a "microtablet".

Preferably, all the mini-tablets of the second formulation have the same composition and have a similar dissolution rate, which is the dissolution rate that can characterize the second pharmaceutical formulation of the invention. This dissolution rate is commonly established on the basis of a unit of the preparation, or in the context of the invention, one gram of microtablets.

The mini-tablets of the second-formulation according to the invention are coated, which makes it possible to mask the taste.

According to one embodiment of the invention, the second formulation comprises from 60% to 70% of potassium bicarbonate, from 15 to 25% of hypromellose, from 7 to 17% of microcrystalline cellulose, from 1 to 3% of glyceryl behenate, from 0.01% to 1% of magnesium stearate, and from 1.5 to 3% of ethyl cellulose, relative to the total weight of the second formulation.

Hypromellose is a hydroxypropyl methylcellulose.

Composition According to the Invention

The composition according to the invention advantageously combines the preferred embodiments of the first pharmaceutical formulation, as described above, and the preferred embodiments of the second pharmaceutical formulation, as described above. In this respect, all possible combinations are envisaged in the context of the invention, as expressed in the claims. For example, the composition according to the invention is preferably such that the Krebs cycle precursor salt is a citrate salt, even more preferably potassium citrate, and such that the bicarbonate salt is potassium bicarbonate.

According to the invention, the patient generally ingests several tablets at each administration, depending on the therapeutic dose that is appropriate for the patient (daily dose divided by the number of administrations per day).

In all cases, one administration of the medicament corresponds to several microtablets and several mini-tablets, i.e. a set of microtablets and mini-tablets.

The invention therefore also covers a set of microtablets and mini-tablets, corresponding to a therapeutic dose. A person skilled in the art is able to evaluate the number of microtablets and mini-tablets corresponding to a therapeutic dose, in relation to the needs of the person, their age, their weight, as a function of the quantity of Krebs cycle precursor salt per microtablet and of bicarbonate salt per mini-tablet, as well as the number of administrations per day.

The pharmaceutical composition according to the invention is in the form of first-formulation microtablets, and second-formulation mini-tablets, i.e. a set of tablets of two different types.

However, a preferred embodiment according to the invention is when the second-formulation tablets are microtablets, i.e. when the tablets of the composition are all microtablets. This is true whether the size of the first-formulation microtablets is identical to or different from the size of the second-formulation microtablets. Of course, the preferred case is the case when the size of the first-formulation microtablets is identical to the size of the second-formulation microtablets. In all cases, the active ingredients—the Krebs cycle precursor salt and the bicarbonate salt—are present in the composition at a physiologically effective dose or representing a multiple or a sub-multiple of an effective dose for a standard patient.

This represents levels of active ingredients, by weight relative to the total weight of the composition, that are significant relative to what is known. This advantageously makes it possible to minimize the volume of the pharmaceutical composition, and therefore the volume taken daily. Consequently, this results in better acceptance by the patient.

This is particularly beneficial for taking the composition at high dosage and/or for paediatric therapeutic treatments.

Owing to the small size of the microtablet, a single microtablet of each of the two formulations is not generally sufficient for one dose, and for each dose, several microtablets of each of the two formulations are administered. One of the advantages of the form as several microtablets is that the patient finds them easier to take, relative to taking a single tablet with a larger volume. This is particularly advantageous when the patient is a child.

The composition according to the present invention can be used in mammals, more specifically in humans, and preferably in children.

The composition according to the invention has the particular feature of continuous, sequential release of the Krebs cycle precursor salt and of the bicarbonate salt all the way along the digestive tract. Thus, firstly, the Krebs cycle precursor salt is released in the stomach, absorbed mainly in the duodenum, and excreted in the urine, where, when it is a citrate salt, it partly forms a complex with the calcium in the urine, preventing the formation of calculi of calcium phosphate and of calcium oxalate. The bicarbonate salt takes over and prolongs the alkalizing effect as it is absorbed primarily in the rest of the digestive tract: jejunum, ileum and colon, and is excreted in the urine. This results, over time, in a slow and continuous excretion of the alkalizing active ingredients in the urine, causing the urinary pH to be maintained at a value above 7 for at least 8 hours, since the salts are released completely over a period of at least 8 hours after ingestion. This composition can therefore provide alkalization of the patient throughout the night with a single dose (corresponding to a single administration) before going to bed.

The sustained release observed in vitro for each of the two formulations reflects controlled release in the body, which can be verified by measuring the urinary pH of patients treated with this composition.

The composition that the applicant has developed has the advantage that, surprisingly, we do not observe antagonism between the two salts present in the composition, but rather synergy. This is due to the optimized, sequential release of these two salts, the two mechanisms of action of which become complementary. This is a real advance relative to the compositions of the prior art.

Gastric tolerance is improved with the composition according to the invention, relative to the formulations of the prior art, and excessively abrupt alkalosis of the blood is avoided, since the release of alkali is slow, allowing the physiological mechanisms to regulate the blood pH smoothly and without causing effects of painful gastric cramps.

The composition according to the invention is particularly suitable for the prevention and treatment of cystinuria, as it allows the urinary pH to be maintained at the recommended values, more effectively than the formulations of the prior art. It makes it possible to reduce the occurrence of lithiasis and the long-term complications, and to reduce surgical operations.

The composition according to the invention can therefore be used as a medicament, in particular for the treatment and/or prevention of cystinuria. This includes the prevention and/or treatment of the complications associated with cystinuria.

The microtablets and mini-tablets according to the invention are particularly suitable for the treatment and/or prevention of cystinuria, owing to their optimum release profile.

The method of manufacture comprises 4 steps:

The first step is a step of mixing the active ingredient, preferably the single active ingredient, with the other ingredients constituting the tablet core, separately for each of the formulations. Each mixing is carried out in a gravity-fed mixer of the Stuart STR4 type, but can be carried out in any other type of industrial mixer.

The second step is a step of manufacturing the two types of tablets, starting with the two mixtures from the first step, separately for each of the formulations. This second step is generally carried out by a first operation of direct compression in a rotary press, for example for manufacturing microtablets of size 2 mm (of the PR12 type) using six supports each having a head with six punches of 2 mm. This second step then most often comprises a second operation of dedusting of the tablets manufactured in the first operation.

The third step is a step of coating, with the coating agent, of the tablets originating from the second step, separately for each of the formulations. The coating agent is generally applied in the form of solution or of suspension under conditions promoting evaporation of the solvent.

The fourth step is a step of uniform filling of containers, which can be bottles, sachets, capsules, ampoules etc.), with each of the two formulations. This step is carried out according to the respective percentage of each formulation in order to obtain the selected ratio of formulation 1 to formulation 2, for example: 33% of microtablets of formulation 1 and 67% of mini-tablets of formulation 2.

The invention is illustrated in the attached FIGS. 1 to 4, where:

FIGS. 1, 2, 3 and 4 commented upon in Examples 1, 2, 3 and 4 below, respectively.

The following examples illustrate the invention without however limiting it.

EXAMPLE 1

A batch of microtablets of 2 mm size (average diameter) is produced according to the method described above, namely a step of mixing the powders, followed by a compression step, then a coating step. This batch is batch A, and consists of 200 g of microtablets. These microtablets have the following composition:

Potassium citrate (active ingredient, source Dr Paul Lohmann): 66.9%

Microcrystalline cellulose (binder, Ceolus® KG-802 from the company Asahi): 19.7%

Microcrystalline cellulose (binder, Ceolus® UF-711 from the company Asahi): 9.8%

Magnesium stearate (flow agent): 2.0%

Glyceryl behenate (lubricant, commercial reference Compritol® ATO 888 from the company GATTEFOSSE): 0.01%;

Ethyl cellulose polymer (coating agent, commercial reference Ethocel® 20 standard premium from the company Dow): 1.66%.

These microtablets are very well accepted and tolerated by patients. Moreover, they have no taste and are easy to swallow.

Figure 1:
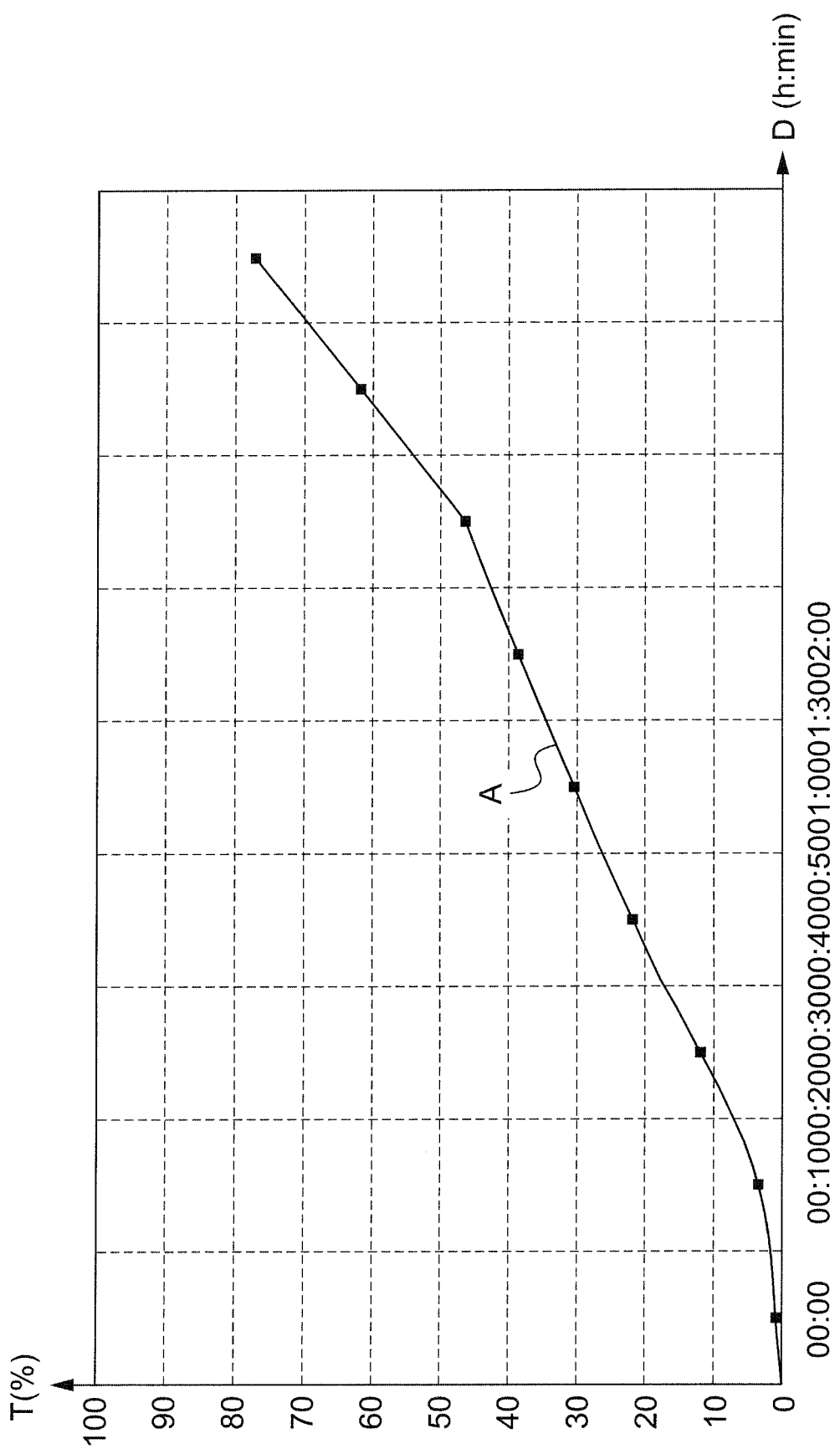
FIG. 1 shows the dissolution profile as the dissolution rate T (percentage of active ingredient—potassium citrate) as a function of time D (h:min) for a first formulation identified by A.

FIG. 1 shows the in vitro dissolution profile of one gram of these microtablets in water, under the conditions described below, over a period of 2 hours. Microtablets A were put in a Pharmatest dissolution apparatus, model PTW S3C, in which the temperature conditions are 37° C.±0.5° C., and the rotary speed is 100 rpm. The dissolution medium is purified water at pH 7. A curve A was obtained, which illustrates the release of potassium citrate, which takes place gradually and evenly. As shown in FIG. 1, the microtablets are able to release the citrate salt in vitro in a dissolution medium of purified water at pH 7 at a rate of 4.5% in 15 minutes, 20.6% in 30 minutes, and 48.6% in one hour.

EXAMPLE 2

A batch I of microtablets with a size (average diameter) of 2 mm was produced according to the method described above, namely a step of mixing the powders, followed by a compression step and then a coating step, at a rate of 200 g of microtablets per batch. These tablets have the following composition:

Potassium bicarbonate (active ingredient, source Dr Paul Lohmann): 66.4%

Hypromellose (matrix, HPMC 100 000 90SH): 19.5%

Microcrystalline cellulose (binder, commercial reference Ceolus® UF-711 from the company Asahi-Kasei): 9.8%

Magnesium stearate (flow agent): 0.01%

Glyceryl behenate (lubricant, commercial reference Compritol® ATO 888 from the company GATTEFOSSE): 2%

Ethyl cellulose (polymer) (coating material, commercial reference Ethocel® 20 standard premium from the company Dow Chemical): 2.3%.

Figure 2:
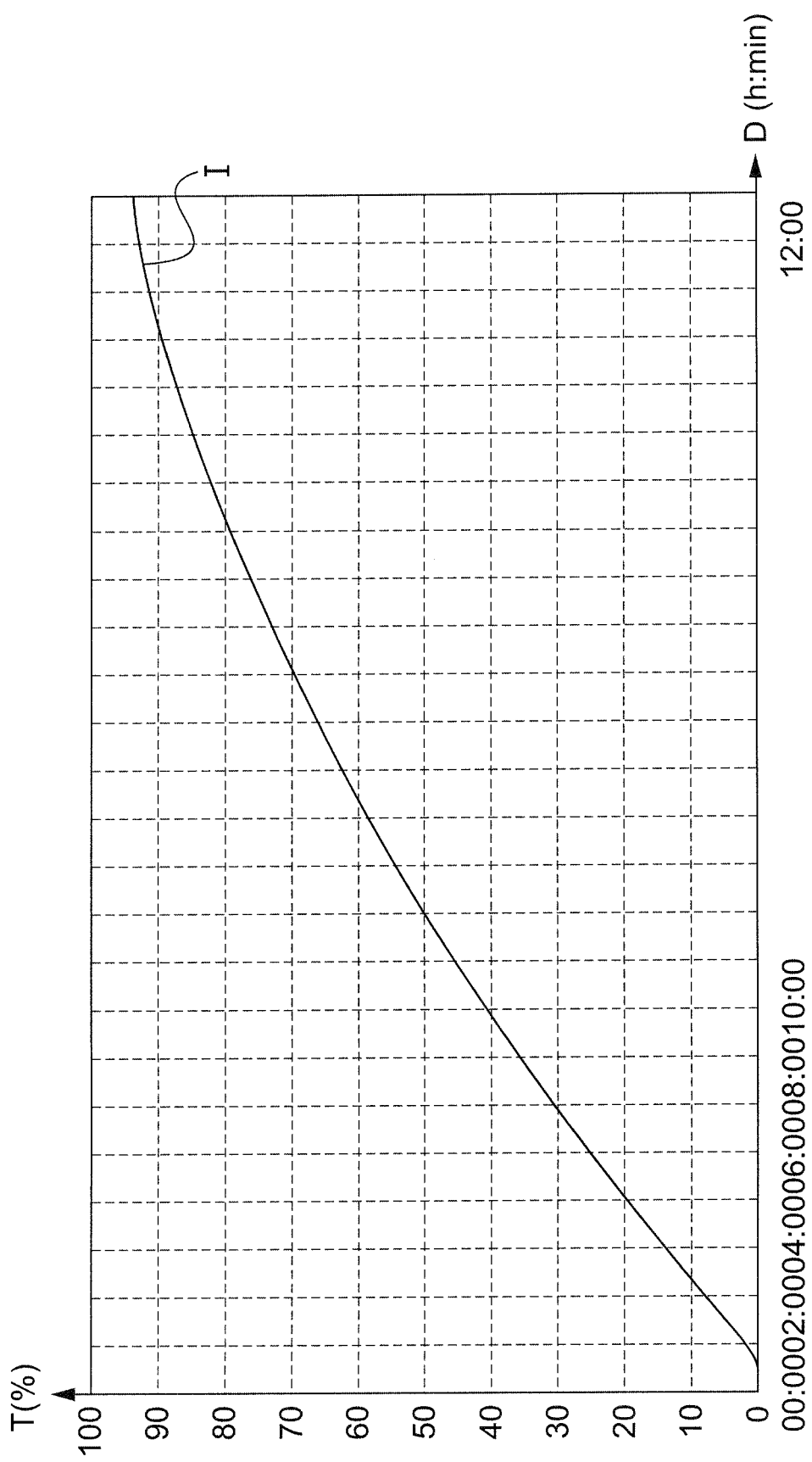
FIG. 2 shows the dissolution profile as the dissolution rate T (percentage of active ingredient—potassium bicarbonate) as a function of time D (h:min) for a composition identified by I.

Curve I in FIG. 2 shows the in vitro dissolution profile of these microtablets in purified water at pH 7.

Such a profile was obtained by placing the mini-tablets in a Pharmatest dissolution apparatus, model PTW S3C, at a temperature of 37° C.±0.5°, with a volume of the dissolution vessel of 1 L and with a rotary speed of 100 rpm.

The potassium bicarbonate is quantified by conductometry according to an analytical method validated according to the ICH recommendations CPMP/ICH/381/95-ICH Q2 (R1).

The microtablets I are very well accepted and tolerated by patients. Moreover, they have no taste and are easy to swallow.

Curve I in FIG. 2 illustrates the release of potassium bicarbonate, which takes place gradually and evenly, meeting the criteria of a rate of at most 50% in 4 hours, at most 75% in 6 hours, and at most 90% in 8 hours.

Moreover, curve I illustrates the release of potassium bicarbonate that leads to almost complete dissolution after 12 to 15 hours.

EXAMPLE 3

A composition according to the invention was prepared, based on one third (in % by weight) of the first formulation from Example 1 and two thirds (in % by weight) of the second formulation from Example 2.

Figure 3:
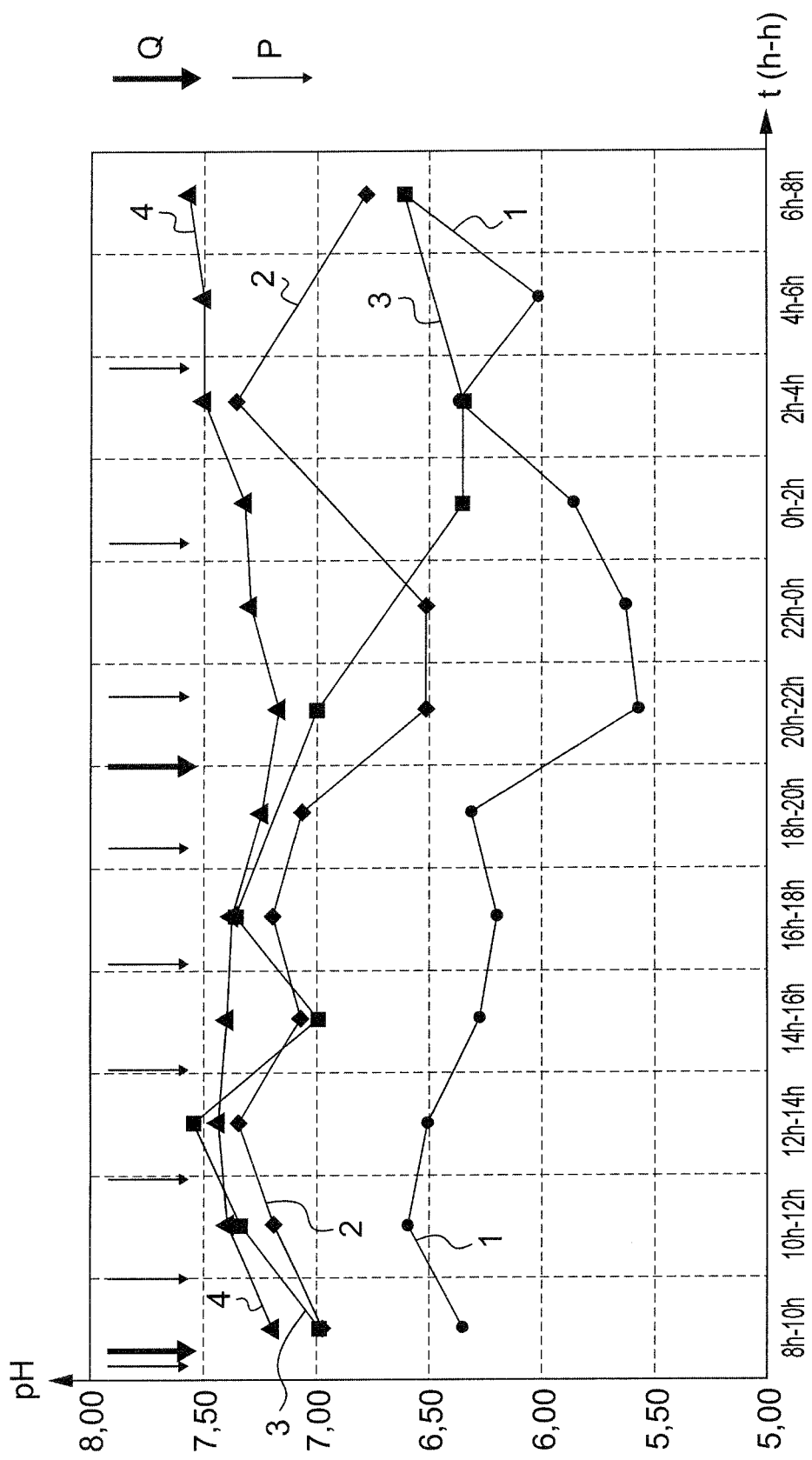
FIG. 3 shows the variations in urinary pH as a function of the hours (h-h) over one day for one subject.

A healthy subject shows a baseline of urinary pH represented in FIG. 3 by curve 1, over one day without treatment.

The subject was following a diet without alcoholic drinks, without carbonated drinks, and reduced in food that contains citric acid (i.e. no drinks of the orange juice type or canned food containing citric acid). Moreover, red meats and cheeses were forbidden.

Three different tests were carried out on this subject (curves 2, 3 and 4). The urinary pH is measured on fresh urine just seconds following micturition with an electrode-type pH meter.

Curve 2 shows the measurements of urinary pH of the patient at regular intervals throughout the 24-hour period for a daily dose of 18 grams in nine administrations (each shown by an arrow P), of citrate in immediate-release officinal formula.

Curve 3 shows the measurements of urinary pH of the patient at regular intervals throughout the 24-hour period for a daily dose of 18 grams in nine administrations (each shown by an arrow P), of potassium bicarbonate in immediate-release officinal formula.

Curve 4 shows the measurements of urinary pH of the patient at regular intervals throughout the 24-hour period for a daily dose of 18 grams in only two administrations (each shown by an arrow Q), of the composition according to the invention.

It can be seen from FIG. 3 that only the composition according to the invention allows the patient's urinary pH to be maintained at values between 7 and 7.6, throughout the day. This is all the more remarkable because just two administrations per day make it possible to achieve such a result.

EXAMPLE 4

The composition of Example 3 was tested on three different healthy subjects (two men referenced 1 and 3, and one woman referenced 2).

Figure 4:
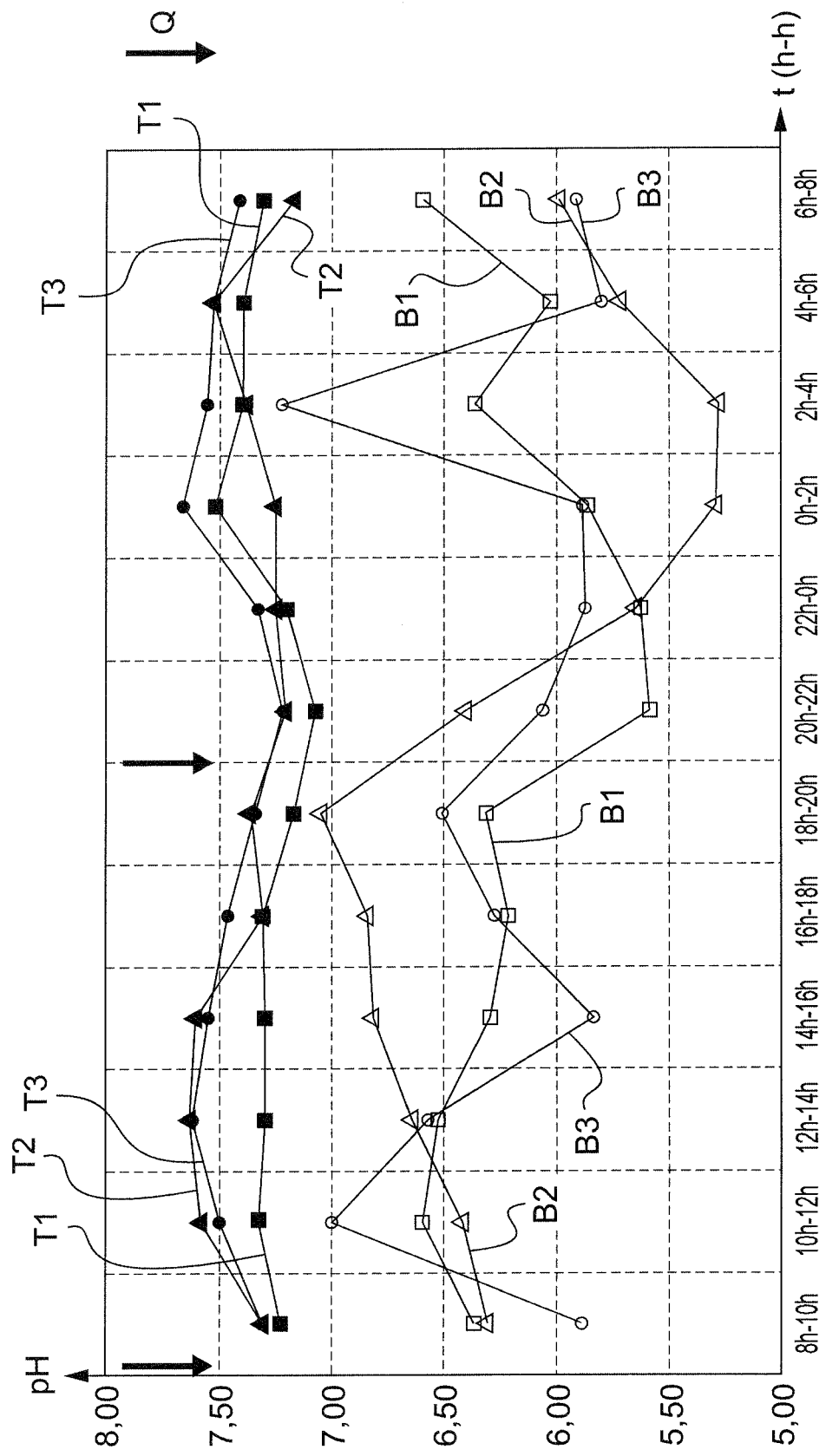
FIG. 4 shows the variations in urinary pH as a function of the hours (h-h) over one day for three other subjects.

FIG. 4 shows the variations of the urinary pH as a function of the time over the course of a day.

For each of these patients i (i=1, 2 or 3), a baseline curve Bi is obtained, for urinary pH over the course of a day without treatment.

Then these healthy subjects were administered two doses per day of the composition according to the invention, one dose of 9 g for each of the two male subjects and of 6 g for the female subject. The urinary pH is measured on the fresh urine just seconds after micturition using an electrode-type pH meter. The subjects were all following the same diet as the subject described in Example 3.

Curves T1 and T2 that are shown represent, for subjects 1 and 2, the mean value of two experiments conducted at an interval of a month under the same conditions.

By measuring the urinary pH while taking the composition according to the invention (curves T1, T2, and T3), relative to a reference without taking medicine (curves B1, B2 and B3), it can be seen that the composition of the invention makes it possible to obtain satisfactory control of urinary pH, in that this pH is never below a value of 7.

The invention claimed is:

1. A solid pharmaceutical composition for oral use in the form of tablets for treating cystinuria, comprising:
   a first solid pharmaceutical formulation for oral use in the form of at least one microtablet, said microtablet being constituted by:
   a core comprising as active ingredient at least one Krebs cycle precursor salt selected from the group consisting of fumarates, malates, citrates, alpha-ketoglutarate, succinyl-coenzyme A, succinates and oxaloacetate, and
   a coating comprising at least one pH independent coating agent selected from the group consisting of ethyl cellulose, paraffin waxes, beeswax, carnauba wax, copolymers of ammonium methacrylate of type A and B, and polyacrylates with dispersion of about 30%,
   wherein the first formulation comprises from 1 to 3% by weight of said at least one coating agent relative to the total weight of the first formulation and has an in vitro dissolution in a dissolution medium buffered at any pH in a range between 1.3 and 7, with a dissolution apparatus of type 2, at a rate from 30 to 50% in 1 hour;

and a second solid pharmaceutical formulation for oral use in the form of at least one mini-tablet, said mini-tablet being constituted by:
a core comprising as active ingredient at least one bicarbonate salt selected from the group consisting of potassium bicarbonate, sodium bicarbonate and magnesium bicarbonate, and at least one sustained-release hydrophilic matrix selected from the group consisting of sodium salts of carboxymethyl cellulose, hydroxypropyl methylcellulose, hydroxypropyl cellulose, hydroxyethyl cellulose, methyl cellulose, the at least one sustained-release hydrophilic matrix being 10% to 30% by weight of the second-formulation; and
a coating comprising from 1% to 20% by weight, relative to the total weight of the second formulation, of at least one pH independent coating agent selected from the group consisting of ethyl cellulose, paraffin waxes, beeswax, carnauba wax, copolymers of ammonium methacrylate of type A and B, and polyacrylates with dispersion of about 30%,
wherein the second formulation has an in vitro dissolution in a dissolution medium buffered at any pH in a range between 1.3 and 7, with a dissolution apparatus of type 2, at a rate of 5% to 15% in one hour.

2. The composition according to claim 1, wherein the composition comprises from 30 to 70% of the first formulation and from 70 to 30% of the second formulation, by weight relative to the total weight of the composition.

3. The composition according to claim 1, wherein the first formulation comprises from 40% to 80% by weight of Krebs cycle precursor salt based on the total weight of the first formulation and the second formulation comprises from 40% to 80% by weight of bicarbonate salt based on the total weight of the second formulation.

4. The composition according to claim 1, wherein the first formulation comprises from 0.01% to 5% of coating agent of the microtablet of the first formulation relative to the total weight of the first formulation.

5. The composition according to claim 1, wherein the first formulation comprises from 55% to 70% of potassium citrate, from 20 to 30% of microcrystalline cellulose, from 0.02% to 2% of magnesium stearate, from 0.01% to 1% of glyceryl behenate and from 1 to 3% of ethyl cellulose, relative to the total weight of the first formulation.

6. The composition according to claim 1, wherein the second formulation comprises from 60% to 70% of potassium bicarbonate, from 15 to 25% of hypromellose, from 7 to 17% of microcrystalline cellulose, from 1 to 3% of glyceryl behenate, from 0.01% to 1% of magnesium stearate, and from 1.5 to 3% of ethyl cellulose, relative to the total weight of the second formulation.

7. A method for treating cystinuria and/or reducing the occurrence of lithiasis and cystinuria, comprising administering to a subject in need thereof and effective amount of the composition according to claim 1.

8. The composition according to claim 2, wherein the first formulation comprises from 40% to 80% by weight Krebs cycle precursor salt based on the total weight of the first formulation and the second formulation comprises from 40% to 80% by weight bicarbonate salt based on the total weight of the second formulation.

9. The composition according to claim 2, wherein the first formulation comprises from 0.01% to 5% coating agent of the microtablet of the first formulation relative to the total weight of the first formulation.

10. The composition according to claim 3, wherein the first formulation comprises from 0.01% to 5% coating agent of the microtablet of the first formulation relative to the total weight of the first formulation.

11. The composition according to claim 1, wherein the Krebs cycle precursor salt is a citrate salt selected from the group consisting of potassium citrate, sodium citrate and magnesium citrate.

12. The composition according to claim 1, wherein the coating agent of the microtablet of the first formulation is a polymer of ethylcellulose.

13. The composition according to claim 1, wherein the at least one bicarbonate salt in the second formulation is potassium bicarbonate.

14. The composition according to claim 1, wherein the coating agent of the second-formulation mini-tablet is a polymer of ethylcellulose.

15. The composition according to claim 1, wherein said sustained-release matrix of the second formulation is a hydroxypropyl methylcellulose.

16. The composition according to claim 1, wherein the second formulation is able to release the bicarbonate salt in vitro in a dissolution medium of purified water at pH 7 with a dissolution apparatus of type 2 at a rate of at most 50% in 4 hours.

* * * * *